(12) United States Patent
Chen et al.

(10) Patent No.: US 9,458,555 B2
(45) Date of Patent: Oct. 4, 2016

(54) CHARACTERIZATION OF MICROARRAYS BY NANOGOLD STAINING

(75) Inventors: Chung-Hsuan Chen, Knoxville, TN (US); Chen-Ren Hsiao, Pingtung (TW)

(73) Assignee: Academia Sinica, Taipei (TW)

( * ) Notice: Subject to any disclaimer, the term of this patent is extended or adjusted under 35 U.S.C. 154(b) by 443 days.

(21) Appl. No.: 12/687,044

(22) Filed: Jan. 13, 2010

(65) Prior Publication Data

US 2010/0184617 A1    Jul. 22, 2010

Related U.S. Application Data

(60) Provisional application No. 61/144,252, filed on Jan. 13, 2009.

(51) Int. Cl.
| | | |
|---|---|---|
| C12M 1/34 | (2006.01) | |
| C12M 3/00 | (2006.01) | |
| C12Q 1/68 | (2006.01) | |
| G01N 33/53 | (2006.01) | |
| C12P 19/34 | (2006.01) | |
| C07H 21/02 | (2006.01) | |
| C07H 21/04 | (2006.01) | |
| A61K 38/00 | (2006.01) | |
| C07K 1/00 | (2006.01) | |
| C40B 30/04 | (2006.01) | |
| G01N 33/58 | (2006.01) | |

(52) U.S. Cl.
CPC ............. *C40B 30/04* (2013.01); *G01N 33/587* (2013.01)

(58) Field of Classification Search
USPC ......... 435/6.1, 6.11, 91.1, 183, 287.1, 287.2, 435/7.1; 436/94, 501; 536/23.1, 24.3, 536/24.33; 530/300, 350; 977/704, 705, 977/727, 728
See application file for complete search history.

(56) References Cited

PUBLICATIONS

Sun et al., Label-free detection of biomolecules on microarrays using surface-colloid interaction. Analytical Biochemistry, 361, 244-252, 2007.*
Battaglia et al., Analysis of DNA microarrays by non-destructive fluorescent staining using SYBR green II. BioTechiques, 29, 78-81, Jul. 2000.*

* cited by examiner

*Primary Examiner* — Frank Lu
(74) *Attorney, Agent, or Firm* — Eckman Basu LLP

(57) ABSTRACT

Methods for determining the quality of a biomolecular microarray to determine suitability of the microarray for performing specific binding reactions, such as hybridization, are provided. Methods are based on staining a microarray with a solution of detectable nanoparticles that reversibly stain the biomolecules through an electrostatic interaction to select microarrays that meet quality standards for hybridization reactions. A gold nanoparticle solution based staining method for DNA microarrays is provided. Destaining methods allowing multiple rounds of hybridization of nanogold stained microarrays are provided. Microarrays selected by methods of the invention are provided.

15 Claims, 8 Drawing Sheets
(8 of 8 Drawing Sheet(s) Filed in Color)

```
                        SEQUENCE LISTING

<160> NUMBER OF SEQ ID NOS: 4

<210> SEQ ID NO 1
<211> LENGTH: 50
<212> TYPE: DNA
<213> ORGANISM: Artificial Sequence
<220> FEATURE:
<223> OTHER INFORMATION: Synthetic sequence

<400> SEQUENCE: 1
agggttttcc cagtcacgac gttgtaaaac gacggccagt gccaagcttg                50

<210> SEQ ID NO 2
<211> LENGTH: 60
<212> TYPE: DNA
<213> ORGANISM: Artificial Sequence
<220> FEATURE:
<223> OTHER INFORMATION: Synthetic sequence

<400> SEQUENCE: 2
tgcatcaaga agtccaccaa aggcgtgctg gacaccacgg gcttcacgtc tccgttggcc     60

<210> SEQ ID NO 3
<211> LENGTH: 60
<212> TYPE: DNA
<213> ORGANISM: Artificial Sequence
<220> FEATURE:
<223> OTHER INFORMATION: Synthetic sequence

<400> SEQUENCE: 3
ggccaacgga gacgtgaagc ccgtggtgtc cagcacgcct ttggtggact tcttgatgca     60

<210> SEQ ID NO 4
<211> LENGTH: 60
<212> TYPE: DNA
<213> ORGANISM: Artificial Sequence
<220> FEATURE:
<223> OTHER INFORMATION: Synthetic sequence

<400> SEQUENCE: 4
tcgcaaaatg cctagatatt atcctactga agatgtgcct cgaaagctgt tgagccacgg     60
```

CHARACTERIZATION OF MICROARRAYS BY NANOGOLD STAINING

CROSS-REFERENCE TO RELATED APPLICATIONS

This application claims priority of provisional patent applications U.S. Ser. No. 61/144,252, titled "Nanogold-Based DNA Microarray Standardization" filed Jan. 13, 2009, the contents of which are incorporated herein in their entirety by reference.

TECHNICAL FIELD OF THE INVENTION

The present invention relates to microarrays. Specifically, the invention relates to characterization of the quality of microarrays prior to hybridization. More specifically, the invention relates to characterization of the quality of DNA microarrays using nanogold staining methods.

SEQUENCE LISTING

This application includes a Sequence Listing submitted herewith via EFS-Web as an ASCII file created on Jan. 12, 2010, named SEQ_LIST_ASN50501US.txt, which is 987 bytes in size, and is hereby incorporated by reference in its entirety.

BACKGROUND OF THE INVENTION

DNA microarray hybridization technology has been applied to various kinds of studies. (Schena, M.; Shalon, D.; Davis, R. W.; Brown, P. O. *Science,* 1995, 270, 467-70). DNA microarray hybridization has been an important and popular tool for broad applications in biomedical research. It is a valuable method for detecting up- or down-regulation of gene expression. In addition to gene expression, other major applications of DNA microarrays include pathogen detection, genotyping, resequencing, drug discovery (Lindsay, M. A. *Nat. Rev. Drug Discov.* 2003, 2, 831-8), pharmacogenomic research [Koch, W. H. *Nat. Rev. Drug Discov.* 2004, 3, 749-61], cancer diagnostics [Cheang, M. C.; van de Rijn, M.; Nielsen, T. O. *Annu. Rev. Pathol,* 2007, 3, 67-97] and protein-DNA interactions [Stoughton, R. B. *Annu. Rev. Biochem.* 2005, 74, 53-82, Heller, M. J. *Annu. Rev. Biomed. Eng.* 2002, 4, 129-53; Gunderson, K. L.; Steemers, F. J.; Lee, G.; Mendoza, L. G.; Chee, M. S. *Nat. Genet.* 2005, 37, 549-54; Gunderson, K. L.; Steemers, F. J.; Ren, H.; Ng, P.; Zhou, L.; Tsan, C.; Chang, W.; Bullis, D.; Musmacker, J.; King, C.; Lebruska, L. L.; Barker, D.; Oliphant, A.; Kuhn, K. M.; Shen, R. *Methods Enzymol.* 2006, 410, 359-76].

Evaluating the activity of various enzymes is essential for understanding of cellular mechanisms, such as intracellular signaling, division and growth processes. Generally, methods of measuring enzymatic activity are performed through antigen-antibody reactions in solution, such as the enzyme-linked immunosorbent assay (ELISA), but chip-based methods have recently been introduced for high-throughput analysis (MacBeath, G. and Schreiber, S. L. 2000, Science, 289, 1760-1763). In particular, a peptide chip has been popularly employed as a screening method of enzyme activity, due to the functional stability, facile synthesis of the substrate, and reproducible binding affinity (Reimer, U., Reineke, U. and Schneider-Mergener, J. Cur. Opi. Biotech. 2002, 13, 315-320). However, the peptide chip also depends mainly on fluorescence or radioisotope-labeled methods in the final analysis step, which are still time-consuming and labor-intensive. In addition, mass spectrometry allows for significant applicability for enzyme assay as a non-labeling method when applied to the peptide chip. Widely used mass spectrometry includes electrospray ionization mass spectrometry (ESI-MS) and matrix-assisted laser desorption/ionization mass spectrometry (MALDI-MS). Technology of applying mass spectrometry to the chip surface typically involves surface-enhanced laser desorption/ionization (SELDI) spectrometry, and the Mrksich's group carried out mass spectrometry for measuring enzymatic activity and screening an inhibitor on the peptide chip using MALDI (Su, J. and Mrksich, M. Angew, Chem. 2002, 114, 4909-4912; D.-H., Tang, W-J. and Mrksich, M. 2004, Nanobiotech. 22, 717-723). Recently, gold nanoparticles (AuNPs) have been applied in various bioengineering fields. Particularly, in the field of mass spectrometry, there has recently been an example in which AuNPs were used as effective matrixes in MALDI (McLean, J. A., Stumpo, K. A. and Russel, D. H. 2005, J. Am. Chem. Soc. 127, 5304-5305). However, this example comprises mixing the gold nanoparticles with a target analyte in solution and then performing measurements on the surface and is not an example in which AuNPs are applied directly on the chip surface.

DNA microarray technology is a powerful tool for comparing levels of expression of large numbers of genes Oligonucleotide or complementary DNA (cDNA) probes are immobilized on solid phases such as modified glass or membrane surface by different technologies [R. B. Stoughton, Ann. Rev. Biochem. 74 (2005) 53-82]. An essential requirement for microarray analyses is that the probe spots be discreet and readily distinguishable from each other. Without this, no valid conclusions can be drawn. As a consequence, analysis of replicate array probes of the same sample is highly preferred in order to draw definitive conclusions about changes in gene expression.

The quality of arrays is critically important due to a large number of genes to be probed and detected on the microarray hybridization chip. DNA probes are first immobilized on the solid phase such as modified glass or membrane surface [Anthony, R. M.; Brown, T. J.; French, G. L. *J. Clin. Microbiol.* 2000, 38, 781-8]. DNA probes on a chip can be prepared either by in-situ synthesis method or spotting DNA segments onto the surface. DNA probes can be immobilized onto solid surface by different technologies such as Pen tip deposition [Yang, A. X.; Mejido, J.; Bhattacharya, B.; Petersen, D.; Han, J.; Kawasaki, E. S.; Puri, R. K. *Mol Biotechnol.* 2006, 34, 303-15], ink-jet deposition [Okamoto, T.; Suzuki, T.; Yamamoto, N. *Nat. Biotechnol.* 2000, 18, 438-41], photolithographic mask [Beier, M.; Hoheisel, J. D. *Nucleic Acids Res.* 2000, 28, e11], and bead array [Steemers, F. J.; Ferguson, J. A.; Walt, D. R. *Nat. Biotechnol.* 2000, 18, 91-4].

Microarray signals are detected by many technologies. Fluorescent labeling and detection is the most popular technique used to identify hybridization signals because it is sensitive and much easier and safer to handle than radioactive labeling methods [Parrish, M. L.; Wei, N.; Duenwald, S.; Tokiwa, G. Y.; Wang, Y.; Holder, D.; Dai, H.; Zhang, X.; Wright, C.; Hodor, P.; Cavet, G.; Phillips, R. L.; Sun, B. I.; Fare, T. L. *J. Neurosci. Methods,* 2004, 132, 57-68]. Sensitive fluorescence detection commonly uses a laser and a confocal microscope, e.g., DNA microarray detector made by Affymetrix Inc., which are typically very expensive and need a trained technician to operate.

Other technologies to detect microarray hybridization are microelectronic arrays [Westin, L.; Xu, X.; Miller, C.; Wang, L.; Edman, C. F.; Nerenberg, M. *Nat. Biotechnol.* 2000, 18, 199-204] and quantum dot methods. Different colors of quantum dots attached to oligonucleotides to hybridize with targets and the signals are detected at specific wavelengths [Han, M.; Gao, X.; Su, J. Z.; Nie, S. *Nat. Biotechnol.* 2001, 19, 631-5; Liang, R. Q.; Li, W.; Li, Y.; Tan, C. Y.; Li, J. X.; Jin, Y. X.; Ruan, K. C. *Nucleic Acids Res.* 2005, 33, e17]. The accuracy is high, but the number of colors available to do hybridization is limited.

Nanoparticles have been recently introduced for detecting DNA microarray hybridization. DNA probes are synthesized on gold nanoparticles and hybridized with DNA on glass surface. The sensitivity of the gold labeling method is almost equal to that of fluorescent labeling [Cao, Y. C.; Jin, R.; Mirkin, C. A. *Science,* 2002, 289, 1757-60; T. A. Taton, C. A. Mirkin, R. L. Letsinger, Science 289 (2000) 1757-1760]. Silver enhancement is usually pursued to amplify the signal. However, skilful handling to prevent overstaining by silver is essential.

Most of microarray quality control studies to date have focused on post-hybridization data quality control rather than on probe spot quality measurements before hybridization. For example, the Microarray Quality Control (MAQC) project of the U.S. FDA is a platform that has been established to help microarray researchers compare inter- or intraplatform microarray results [MAQC Consortium, Shi, L. et al. *Nat. Biotechnol.* 2006, 24, 1151-61]. Bylesjö et al. assessed the cDNA microarray spot quality following hybridization with target genes labeled with Cy5 and Cy3 dyes [Bylesjö, M.; Eriksson, D.; Sjödin, A.; Sjöström, M.; Jansson, S.; Antti, H.; Trygg, J. *BMC Bioinformatics,* 2005, 6, 250-9]. Both methods assess quality after hybridization. Array quality could be used to check the general quality of hybridization, but the studies assume that the qualities of all chips were more or less the same. However, this is a risky assumption. The characterization of microarray spots for each chip is critical before the hybridization step.

Several microarray quality control methods for spots have been used. SYTO® 61 and SYBR® Green II dye staining techniques are array quality control methods before hybridization [Yue, H.; Eastman, P. S.; Wang, B. B.; Minor, J.; Doctolero, M. H.; Nuttall, R. L.; Stack, R.; Becker, J. W.; Montgomery, J. R.; Vainer, M.; Johnston, R. *Nucleic Acids Res.* 2001, 29, e41; Battaglia, C.; Salani, G.; Consolandi, C.; Bernardi, L. R.; De Bellis, G. *BioTechniques,* 2000, 29, 78-81]. These approaches use non-destructive DNA-binding fluorescent dye to stain DNA probes. Only a few slides in each batch are usually tested by these methods because the tested arrays are not available for subsequent hybridization [Shearstone, J. R.; Allaire, N. E.; Getman, M. E.; Perrin, S. *BioTechniques,* 2002, 32, 1051-7]. Wang et al. used TDAV (third dye array visualization) technology to quantitatively evaluate and control every array. [Wang, X.; Jia, S.; Meyer, L.; Xiang, B.; Chen, L. Y.; Jiang, N.; Moreno, C.; Jacob, H. J.; Ghosh, S.; Hessner, M. J. *BMC Bioinformatics,* 2006, 7, 378-87]. The fluorescein isothiocyanate (FITC) labeled DNA probes or oligonucleotides are printed on the array slides and makes prehybridization assessment of array quality possible. [Hessner, M. J.; Singh, V. K.; Wang, X.; Khan, S.; Tschannen, M. R.; Zahrt, T. C. *BMC Genomics,* 2004, 5, 12-22; Hessner, M. J.; Wang, X.; Hulse, K.; Meyer, L.; Wu, Y.; Nye, S.; Guo, S. W.; Ghosh, S. *Nucleic Acids Res.* 2003, 31, e14]. The advantage of the method is to eliminate substandard arrays before experiments. Probe retention rate can also be monitored, but to label DNA probes with fluorescence dyes is expensive and tedious. The detection also needs expensive confocal laser scanners to avoid overlap of the emission wavelengths of fluorochromes used in sample detection such as Cy3 or Cy5 [Yang, A. X.; Mejido, J.; Bhattacharya, B.; Petersen, D.; Han, J.; Kawasaki, E. S.; Puri, R. K. *Mol. Biotechnol.* 2006, 34, 303-15]. An electrochemical immunoassay has been developed using a colloidal gold label that, after oxidative gold metal dissolution in an acidic solution, was indirectly determined by anodic stripping voltametry (ASV) at a single-use carbon-based screen-printed electrode (SPE). [Dequaire, M.; Degrand, C.; Limoges, B. *Anal. Chem.* 2000, 72, 5521-5528.]

A need exists in the art to address the aforementioned deficiencies and inadequacies, especially in connection with development of methods for characterization of chips prior to DNA microarray hybridization. As of this invention, there were no chips that allow both quality analysis and hybridization using the same chip. It is risky to draw conclusions from results of different chips if there is no knowledge of the quality of the chips before hybridization, even if they are from the same batch.

Due to the high cost and labor involved in fabricating microarrays, there also is a need for methods that allow multiple rounds of use of a microarray chip. Typically, hybridization reactions on a microarray surface are detected by staining. There exists a need for methods that allow destaining of a hybridized chip in a manner that render the destained chips suitable for subsequent rounds of hybridization reactions.

SUMMARY OF THE INVENTION

This invention provides a colorimetric method for performing quality control on an array. In one aspect, the quality analysis of probe spots can be obtained by using gold nanoparticles with positive charges to label negatively charged DNA through electrostatic attraction. The probe spots can be detected by a simple personal computer scanner. Gold nanoparticles deposited on DNA probes bound to a glass surface can be destained by dissolving in bromine-bromide solution. The same microarray treated with gold particles staining and destaining can still be used for hybridization with nearly the same efficiency. This approach makes quality control of a microarray chip feasible and should be a valuable tool for biomarker discovery in the future.

The method for destaining by dissolving the gold nanoparticles in bromine bromide solution can also be applied for reusing hybridized microarrays stained with gold nanoparticles. Nanogold-stained hybridized microarrays are destained by dissolving the gold particles with bromine-bromide solution according to the disclosed invention. The destained microarrays are then available for subsequent rounds of hybridization analysis. The process can be repeated any number of times as long as the hybridized microarrays are stained with gold nanoparticles.

In general, the invention is directed to a method for determining a quality of a microarray comprising biomolecules immobilized at discrete locations on the microarray surface, to determine suitability of the microarray for performing a specific binding reaction, the method comprising the steps of: (a) contacting the microarray with a solution comprising detectable nanoparticles under conditions wherein the detectable nanoparticles reversibly stain the biomolecules through an electrostatic interaction; (b) detecting a signal dependent on the staining interaction, wherein the signal indicates a presence of the biomolecules immobilized on the microarray surface; and (c) destaining the microarray to obtain a microarray suitable for performing the specific binding reaction. In some embodiments the method further comprises (d) using the specific microarray whose quality has been determined for performing the specific binding reaction.

In some embodiments, the biomolecules are selected from the group consisting of: DNA, RNA, oligonucleotides, peptides, proteins and biopolymers. In a preferred embodiment, the detectable nanoparticles are gold nanoparticles.

In one aspect the selected staining conditions comprise solution pH and solution ionic strength suitable for electrostatic binding of the detectable nanoparticles to the biomolecules.

In one aspect, detecting the signal further comprises assessing a quality of the stained microarray and optionally selecting a microarray which meets a predetermined standard of quality. In some embodiments, the predetermined standard of quality is selected from the group consisting of: an intensity of stain at each discrete location on the microarray, a uniformity of stains at various locations on the microarray, and a lack of stained biomolecules at one or more locations on the microarray.

The method of claim 1, wherein the specific binding reaction is performed prior to the steps of determining the quality of the microarray, wherein the specific binding reaction is reversible.

The invention also relates to methods for determining a quality of a microarray comprising nucleic acids immobilized at discrete locations on the microarray surface, to determine suitability of the microarray for performing a hybridization reaction, the method comprising the steps of: (a) contacting the microarray with a solution comprising gold nanoparticles under conditions wherein the nanoparticles reversibly stain the nucleic acids; (b) scanning the microarray for presence of the nucleic acids on the microarray surface at amounts sufficient to meet a minimum quality standard; (c) selecting a microarray that meets the quality standard; and (d) destaining the miroarray to obtain a microarray suitable for performing the hybridization reaction. In some aspects the method further comprises: (e) using a microarray that met a minimum quality standard in a hybridization reaction.

In some embodiments, the size of the probe immobilized on the microarray is at least 2× shorter than the target nucleic acid used in the hybridization reaction.

In some aspects the method comprises: the step of performing a prehybridization reaction before the hybridization reaction. In some aspects, the method comprises the step of performing the determination of the quality of the microarray after a prehybridization reaction but before the hybridization reaction.

In one embodiment, the destaining step uses a bromine-bromide solution. In a preferred embodiment, the bromine-bromide solution is about $10^{-4}$M $Br_2$ in about 1M HBr.

In some aspects the nucleic acid probe on the microarray is selected from the group consisting of DNA, RNA, microRNA, dsRNA, small interfering RNA (siRNA), peptide nucleic acid (PNA), oligonucleotide, and synthetic oligonucleotide.

In some aspects the staining solution comprises a cationic gold solution comprising amino groups on its surface. In some embodiments the gold solution is a colloidal solution.

In some aspects the minimum standard of quality is selected from the group consisting of: an intensity of stain at each discrete location on the microarray, an uniformity of stains at various locations on the microarray, a lack of homology spots, and missing spots at one or more locations on the microarray.

In some aspects the microarray is homemade or commercially available.

The invention also relates to a microarray selected to meet the quality standard by any method described herein.

The invention also provides a destaining method for using a nucleic acid microarray in a plurality of successive hybridization reaction, the method comprising the steps of: staining a microarray comprising target nucleic acids hybridized to complementary nucleic acid probes immobilized on a surface of the microarray with gold nanoparticles; optionally, visualizing the stained pattern on the microarray; and destaining the microarray by dissolving the gold particles with a bromine-bromide solution, wherein the destained microarray is suitable for a subsequent round of hybridization reaction analysis. In one embodiment, the bromine-bromide destaining solution is about $10^{-4}$M $Br_2$ in about 1M HBr.

In some embodiments, the method further comprises the step of hybridizing the destained microarray with target nucleic acid.

In some embodiments, the method further comprises one or more of the steps of prehybridization or post-washing of the hybridized microarray prior to staining with gold nanoparticles.

In some embodiments, the target nucleic acid is denatured DNA.

One aspect of the invention relates to nanogold-based DNA microarray standardization. A method for standardizing a DNA microarray prior to performing a hybridization reaction includes the following steps: (a) staining a DNA microarray with a cationic nanogold particle to obtain an array with a staining signal; (b) assessing the staining signal to select a DNA microarray that meets a quality standard; and (c) destaining the DNA microarray to obtain a qualified, non-stained DNA microarray.

Another aspect of the invention relates to a kit for standardizing a DNA microarray comprising: (a) chloroauric acid; (b) a bromine-bromide solution; and (c) instructions for use of the kit for standardization of nucleic acid chips.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1A is a scanned image of an oligonucleotide probe-immobilized microarray that is the first time stained with nanogold particles. FIG. 1B is a scanned image of the same microarray of FIG. 1A that is the third time stained with nanogold particles.

FIG. 2A is a scanned image of a hybridized microarray that is the first time stained with nanogold particles. FIG. 2B is a scanned image of the same microarray of FIG. 2A that is the second time stained with nanogold particles. Lane 1: probe TAF2H printed; lane 2: printed with spotting solution; lane 3: probe PC101 printed, which was complementary to the target DNA.

FIG. 3A shows fluorescent signal detected from Cy5 signal. FIG. 3B shows gold nanoparticles used to stain the array.

FIG. 5A shows the first staining result. FIG. 5B shows the same array staining after the second time.

FIG. 7A shows staining obtained after dissolution of gold particles. FIG. 7B shows staining obtained after prehybridization.

DETAILED DESCRIPTION OF THE INVENTION

Figure 1:
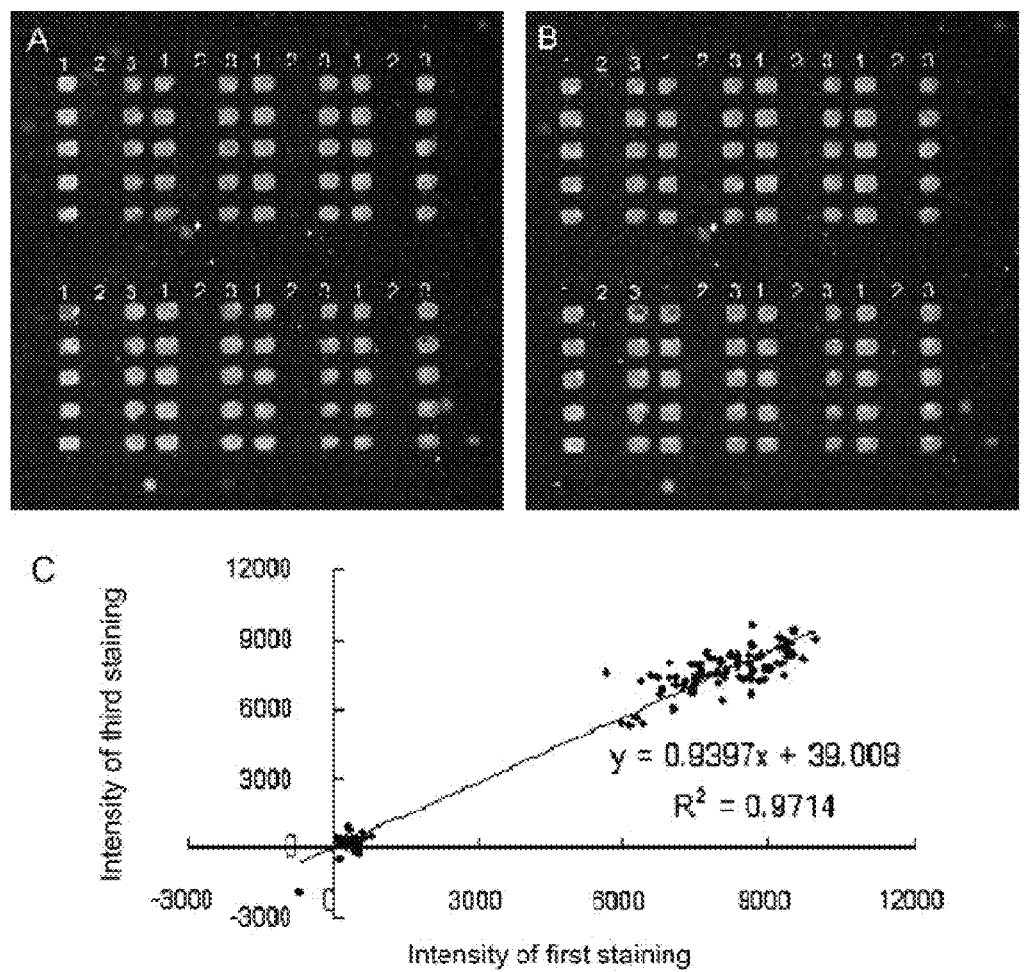
FIGS. 1A-1B show staining of probes on the immobilized arrays.
FIG. 1C is a graph showing an intensity correlation of the FIG. 1A and FIG. 1B staining results as 0.99 ($R^2$=0.9714).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The invention provides a method to achieve quality examination of microarrays while still allowing the same arrays to be used for hybridization. The nanogold on a stained DNA microarray could be dissolved with bromine-bromide treatment. The same array after destaining was subjected to hybridization and gold staining. This qualitative examination was simple and reliable, and it needed only an inexpensive PC scanner detector. Because a flatbed scanner can easily detect a spot size of approximately 100 µm, this approach should be able to reach the sensitivity of 1 fmol or less with a simple flatbed PC scanner detector. The method can also be used in homemade and commercial microarrays. It can be applied to direct hybridization between probe DNA and mRNA without the need for PCR because of the charge-charge interaction for detection. Better quantitative measurement should also be expected.

The invention is related to a colorimetric method for quality control of an array. The quality analysis of probe spots is obtained by using gold nanoparticles' positive charges to label DNA through electrostatic attraction. The spots may also be detected by a personal computer scanner. Gold nanoparticles deposited on glass surface may be dissolved in a bromine-bromide solution. The same microarray treated with gold particles staining and de-staining may still be used for subsequent hybridization reactions without diminished efficiency. This approach makes quality control of individual microarray chips feasible.

Because DNA microarray chips are very expensive, the method disclosed in this invention is to assure the quality of DNA chips in a cost-saving and time-efficient manner. The method of the invention uses positively charged gold nanoparticles to detect DNA microarray hybridization. Commercially available positively charged gold nanoparticles, which are coated with amino groups on the surface can be used. [Sun, Y.; Fan, W. H.; McCann, M. P. Golovlev, V. *Anal. Biochem.* 2005, 345, 312-9]. Cationic nanogold labels anionic DNA due to a charge-charge interaction. Gold particles that deposit on the surface of DNA chips are visible. The technique is easy to perform with sensitivity comparable to fluorescent dye labeling method. Id. The approach is simple and the detection may be achieved by a simple personal computer scanner, which costs much less than a laser scanner.

The method of the invention can be used as a platform for microarray users to compare the data to those from different laboratories and different array systems to obtain actual results.

The method uses 250 nm gold nanoparticles that are coated with positively charged functional groups on the surface to stain arrays without silver enhancement [Cao, Y. C.; Jin, R.; Mirkin, C. A. *Science,* 2002, 289, 1757-60]. Cationic gold particles attract to the anionic DNA or RNA molecules resulting in the deposition of gold particles on the surface. The results are visible and may be scanned directly by a high-performance flatbed scanner rather a laser scanner. Gold nanoparticles are soluble in a bromine-bromide solution, which converts $Au^0$ into $Au^{3+}$ [Dequaire, M.; Degrand, C.; Limoges, B. *Anal. Chem.* 2000, 72, 5521-8]. The method combines these two steps to analyze a spotted array before hybridization. The same array may then be used for performing subsequent hybridization.

Oligonucleotide probes immobilized on glass surface and labeled with positively charged gold nanoparticles are visible to the naked eye. In bromine-bromide solution gold particles can be oxidized and form Auric ions ($Au^{3+}$) and thus become soluble [Shearstone, J. R.; Allaire, N. E.; Getman, M. E.; Perrin, S. *BioTechniques,* 2002, 32, 1051-7].

While the present disclosure is directed to the analysis of the quality of nucleic acid-based microarrays by binding with gold nanoparticles, the underlying methodologies for determining charge phenomena on solid-liquid interface can be adopted for the analysis of interaction of colloidal particles and biopolymers tethered on the surface of a microarray. Models for describing surface charge on a microarray surface are known, such as the Gouy-Chapman-Stern-Graham model. [Behrens S H, Grier D G. J Chem Phys. 2001; 115(14):6716-6721]. These models predict selective binding of colloidal particles to target molecules at a certain range of solution pH and solution ionic strength. An initial analysis of the optimal pH range for selective binding of nanoparticle and bio-polymers on a solid substrate can be performed by taking into consideration the chemical composition and the density of chemical groups on the substrate, as well as the composition and the size of the probe and target molecules. [Su, Y. et al. Anal Biochem. 2007 Feb. 15; 361(2): 244-252.] The models can be applied for determination of experimental conditions for characterization of the quality of microarrays comprising peptides, proteins and other biopolymers (in addition to nucleic acids), using detectable nanoparticles for staining and destaining as disclosed herein.

For example, when the interaction of bovine serum albumin (BSA) with gold colloids and surfaces was studied to determine the surface charge and coverage, the results suggested that BSA binding to gold nanoparticles and gold surfaces occurs by an electrostatic mechanism when citrate is present. [Brewer S H, Glomm W R, Johnson M C, Knag M K, Franzen S. Langmuir. 2005 Sep. 27; 21(20):9303-9307].

Prestaining an immobilized array by gold particles can eliminate defective arrays or non-homogenous spots. The same array could be used to do hybridization after dissolving gold particles. One could also acquire the intensity data of each spots before hybridization to compare with that after hybridization.

Staining with gold nanoparticles before hybridization provides a cost-efficient method to obtain characterization of a spotted array. Gold nanoparticles deposited on the array surface could be dissolved by bromine-bromide solution. The same array could be used to hybridize with target DNA. The technique was easy to operate and requires no expensive instruments. In conclusion, the method of using gold nanoparticles staining and bromine-bromide solution dissolving to qualify DNA microarrays is an easy and inexpensive way to perform array quality control. The technique makes quality control and hybridization on each array possible.

The bromine-bromide destaining methods for dissolving gold nanoparticles disclosed herein can be applied towards allowing the use of a nucleic acid microarray in a plurality of successive hybridization reactions. The method comprises the steps of: staining a microarray comprising target nucleic acids hybridized to complementary nucleic acid probes immobilized on a surface of the microarray with gold nanoparticles; optionally, visualizing the stained pattern on the microarray; and destaining the microarray by dissolving the gold particles with a bromine-bromide solution, wherein the destained microarray is suitable for a subsequent round of hybridization reaction analysis. In one embodiment, the bromine-bromide destaining solution is about $10^{-4}M$ $Br_2$ in about 1M HBr.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Probe Spotting and Immobilization

Probes with the desired sequences, as used by Sun and coworkers [Sun, Y.; Fan, W. H.; McCann, M. P. Golovlev, V. *Anal. Biochem.* 2005, 345, 312-9], were synthesized (MDBio, Taipei, Taiwan) and dissolved in deionized water at a concentration of 2.0 µM. The sequences of the probes are listed in Table 1. The samples were dissolved in deionized water, followed by mixing with equal volume of 99.5% dimethyl sulfoxide (DMSO) to 1 µM. The mixed probes were spotted onto Corning Ultra-GAPS slides (Corning, Acton, Mass., USA) with the SpotBot Personal Microarrayer (TeleChem International, Sunnyvale, Calif., USA). The delivery volume for each spot was estimated to be 12.5 nl with spot diameter of approximately 600 µm. The quantity of the probe DNA was estimated to be 12.5 fmol. The spotted arrays were vacuum-dried at room temperature overnight. The probes were immobilized onto the slide surface by an ultraviolet (UV) crosslinker (CL-1000, UVP, Upland, Calif., USA) with UV energy of 600 mJ.

TABLE 1

| Probe | Sequence | SEQ ID NO. |
|---|---|---|
| PC101 | 5'AGGGTTTTCCCAGTCACGACGTTGTAAAACGACGG CCAGTGCCAAGCTTG 3' | 1 |
| TAF2Ht | 5'TGCATCAAGAAGTCCACCAAAGGCGTGCTGGACAC CACGGGCTTCACGTCTCCGTTGGCC 3' | 2 |
| TAF2H | 5'GGCCAACGGAGACGTGAAGCCCGTGGTGTCCAGCA CGCCTTTGGTGGACTTCTTGATGCA 3' | 3 |
| RPL6 | 5'TCGCAAAATGCCTAGATATTATCCTACTGAAGATG TGCCTCGAAAGCTGTTGAGCCACGG 3' | 4 |

Example 2

Nanogold DNA Labeling and Staining

Gold nanoparticle-staining of DNA microarrays was performed by using a protocol provided in the staining kit AG12 (Sci-Tec, Knoxville, Tenn., USA). Cationic nanogold particles attract negatively charged DNAs due to charge-charge interactions. Briefly, 10 µl of gold colloids and 4 µl of activator were mixed and left the solution standing for 1 min, followed by the addition of 500 µl of buffer. The gold solution was transferred to an array surface with 18×18 mm$^2$ area and incubated for 10 min at room temperature. The slide was rinsed in water and air-dried. Gold particles that were aggregated from 250-nm nanoparticles on hybridization spots were clearly visible. All staining results were scanned and analyzed by an Auro-Gen Microarray System (Sci-Tec), which consisted of a modified personal computer scanner with software for data analysis.

Nanogold-stained arrays were incubated in a 1-ml bromine-bromide solution with $10^{-4}$ M $Br_2$ in 1 M HBr for 10 min to dissolve gold particles. The slides were subsequently washed thoroughly by deionized water and dried with air. These bromine-bromide-treated arrays were used for subsequent experiments.

Example 3

Nanogold DNA Dissolution

To dissolve nanogold-DNA labeling and staining, nanogold-stained arrays were incubated with 1 ml bromine-bromide solution ($10^{-4}$M $Br_2$ in 1M HBr) for 10 min. The slide was washed thoroughly with deionized water and air dried.

Example 4

Array Hybridization

Array prehybridization was processed with the following procedures. Incubation of the array was performed in a buffer containing 5× saline sodium citrate (SSC) and 0.1% sodium dodecyl sulfate (SDS) with 0.1% bovine serum albumin (BSA) at 42° C. for 20 min. The array was subsequently washed with deionized water twice and then allowed to air dry.

Hybridization was completed as follows. The target double stranded DNA, M13mp18, was denatured at 95° C. for 10 min and then cooled on ice immediately for 5 min. The size of M13mp18 was 7250 bp. Samples were prepared with approximately 600 fmol of denatured DNA mixed with 10 µl of Pronto! Universal Hybridization Buffer (Corning). The total volume of the mixture was 20 µl. The mixture was pipetted onto the array surface and covered with a glass cover slip. Hybridization was performed at 42° C. overnight. After hybridization was completed, the slide was washed with 2×SSC and 0.1% SDS at 42° C. for 5 min and with 0.1×SSC at room temperature twice for 2 min. The array was then dried by compressed air and stained by gold nanoparticles.

Example 5

Applicability to Commercial Array Detection

Figure 5:
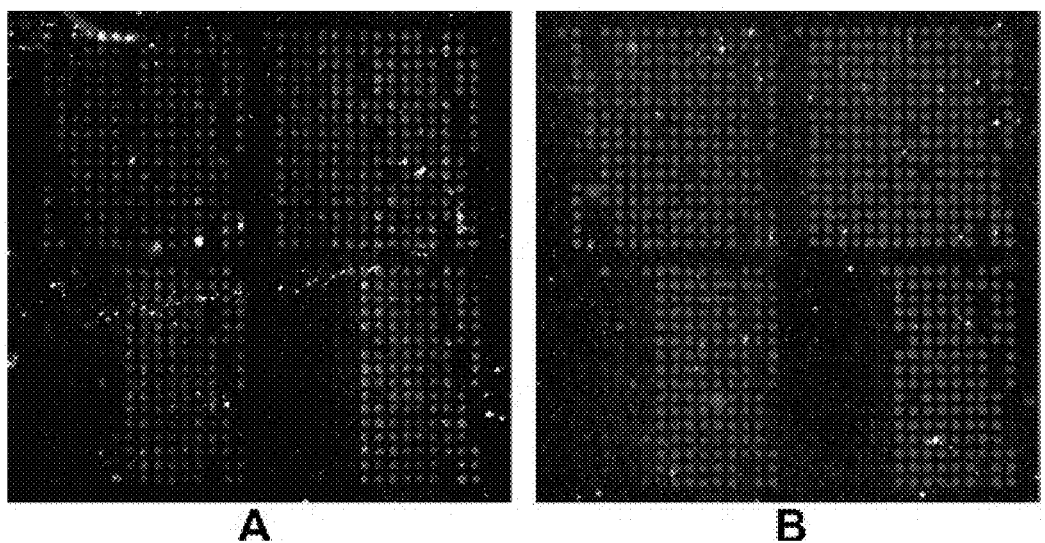
FIGS. 5A-5B SHOW commercial miRNA microarrays successfully stained by gold nanoparticles. Gold nanoparticles stained the array for 8 min. The spots were clear, and the array pattern was the same as the pattern by the producer.

A microRNA (miRNA) microarray (NCode Multi-Species miRNA Microarray, Invitrogen, Carlsbad, Calif., USA) was used to stain with gold nanoparticles. The array was treated with prehybridization solution at 42° C. for 20 min to wash away the solution for spotting process. The array was washed with deionized water twice and allowed to air dry. Positively charged gold nanoparticles were used to stain the array, and the array was detected by a PC scanner detector as described previously (FIG. 5). The pattern was roughly the same between the first and second stainings. Therefore, it indicated that our method of microarray staining by gold particles and destaining by bromine-bromide solution can be applied to commercially-available spotted microarrays.

Example 6

Repeated Staining of Arrays

It was discovered that repeatedly staining and stripping of nanogold particles from DNA arrays were feasible. Gold particles deposited on array surfaces were stable and directly visible without using a laser scanner (FIG. 1A). The staining results were scanned by an inexpensive flatbed scanner and analyzed by imaging software for quantitative analysis of aggregates of gold nanoparticles. A gold dissolving solution, $10^{-4}$ M $Br_2$ in 1M HBr, was added to dissolve gold particles on slides for 10 min. This staining-dissolution process was repeated three times. The very same array was stained and destained three times, and the results after the first and third stainings are shown in FIGS. 1A and B, respectively. The third staining (FIG. 1B) was as strong as the first one (FIG. 1A), with a spot intensity correlation coefficient of more than 0.99 ($R^2$>0.97) (FIG. 1C). The result indicated that the treatment of a gold nanoparticle-stained array with bromine-bromide solution to remove gold nanoparticles had little or no impact on the subsequent gold particle-staining efficiency.

The concentration ratio of $Br_2$/HBr may be adjusted. It was found that if the concentration of HBr was too low, the concentration of $Br_2$ must be raised, which would impact the results of hybridization, increase background noise, and even lose spots signals. If the concentration of HBr was increased, the background noise of DNA array after hybridization would increase and make spots signals invisible The measurement of gold staining is due to the aggregation of nanogold into a micrometer size cluster. It is based on the colorimetric measurement similar to colloidal suspensions when colloid particles aggregate. It has a good linear relationship between the intensity and the quantity of nanoparticles. These results confirmed that staining of microarrays with gold nanoparticles and destaining with bromine-bromide solution to remove the gold nanoparticles did not change the staining efficiency of the gold particles. Because gold nanoparticles are dissolved during the interaction with bromine-bromide solution, these gold nanoparticles cannot be used again for labeling.

Example 7

Staining-Destaining Applied to Hybridized DNA Microarray

Figure 2:
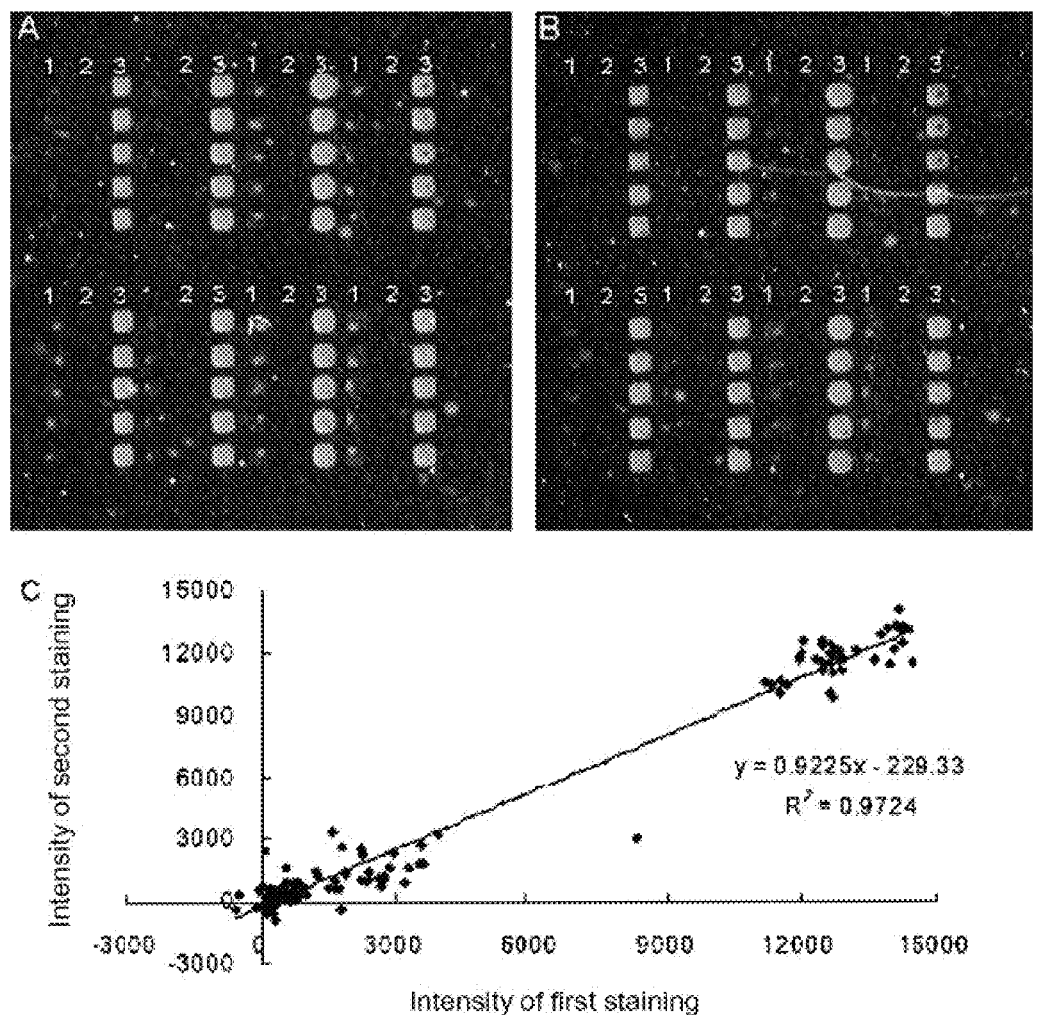
FIGS. 2A-2B show results of repeated staining and destaining by gold nanoparticles process applied to a hybridized array. The hybridized array was stained ly.
FIG. 2C is a graph showing an intensity correlation of the FIG. 2A and FIG. 2B staining results as 0.99 ($R^2$=0.9714).

As shown in FIG. 2A-2C, the gold dissolving solution could be used on a hybridized array. The staining and destaining process could also be applied to a hybridized array. The DNA microarray was hybridized with denatured DNA targets at 42° C. overnight. After hybridization and postwashing, the array was stained by nanogold. Signals for the spots with complementary targets were clearly visible, whereas spots with noncomplement targets were not observed (FIG. 2A). Bromine-bromide solution was then added to the array surface to dissolve and remove the gold particles. The same array was then stained by gold particles. The staining result was approximately the same as the first staining (FIG. 2B). The intensity coefficient correlation of these two staining results was greater than 0.99 (R2>0.97) (FIG. 2C). Repeated staining and destaining processes did not hurt the next staining efficiency for hybridized DNA.

Figure 3:
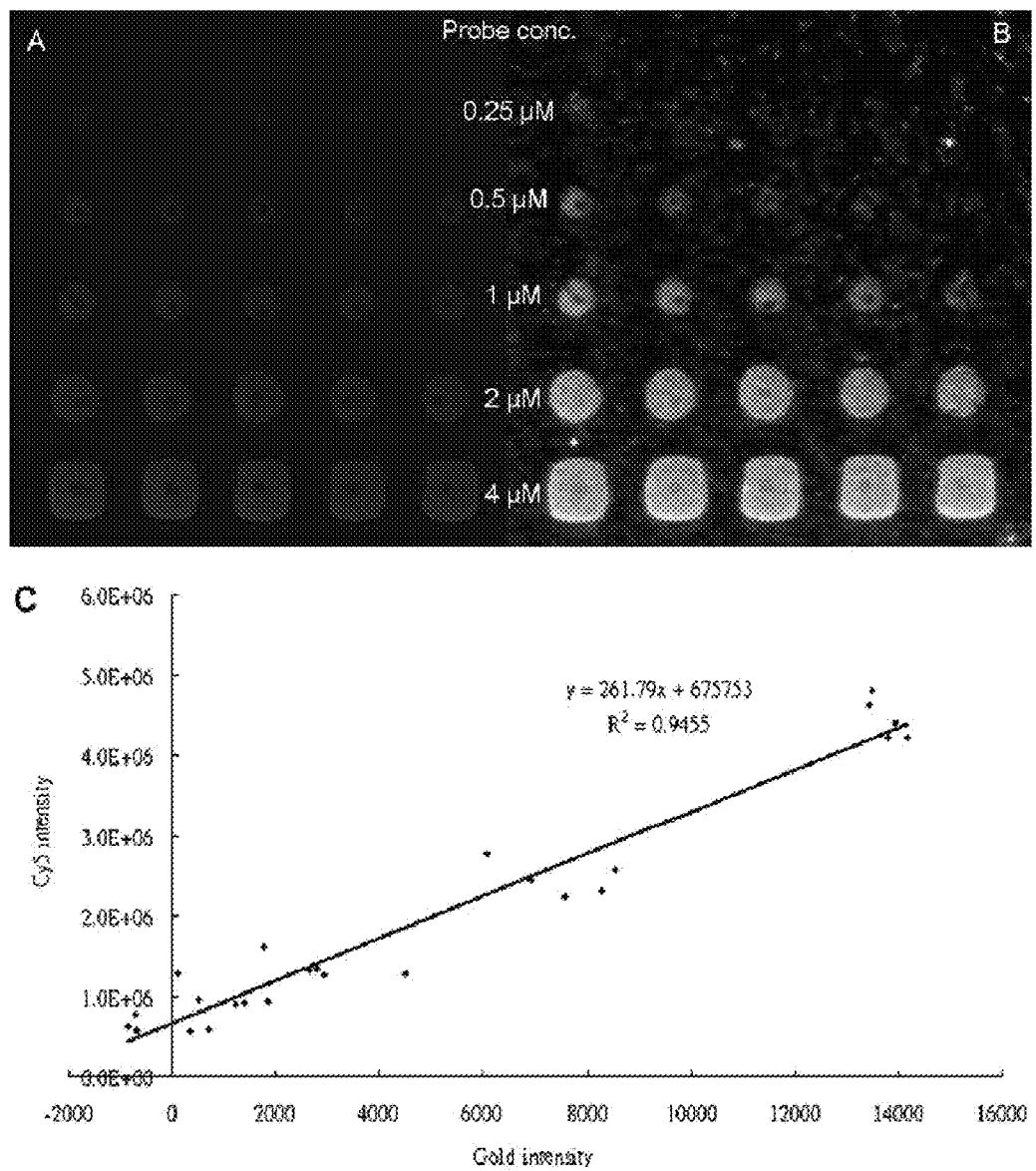
FIGS. 3A-3B show comparison of fluorescent detection to gold staining detection of each spot hybridized with complementary DNA. Probes, which are 60mer oligonucleotides, were spotted on glass surface with a concentration range from 0.25 to 4 µM. Cy5-labeled, 700-fmol, and 7250-nt denatured PCR products were hybridized to the array.
FIG. 3C shows spot intensities by fluorescent and gold signals for each spot. The regression line and $R^2$ (=0.9455) are shown.

Target DNA labeled with Cy5 was used for hybridization. After hybridization, the fluorescent intensity was detected by a fluorescence detector. The array was also stained by gold nanoparticles and detected by the gold signal. To compare the fluorescent intensity and gold intensity, the coefficient correlation was 0.97 (R2>0.94). The detection limits in the hybridization with Cy5 and gold staining were comparable (FIG. 3).

Example 8

Identification of Poorly Fabricated Arrays for Quality Control (QC)

Figure 4:
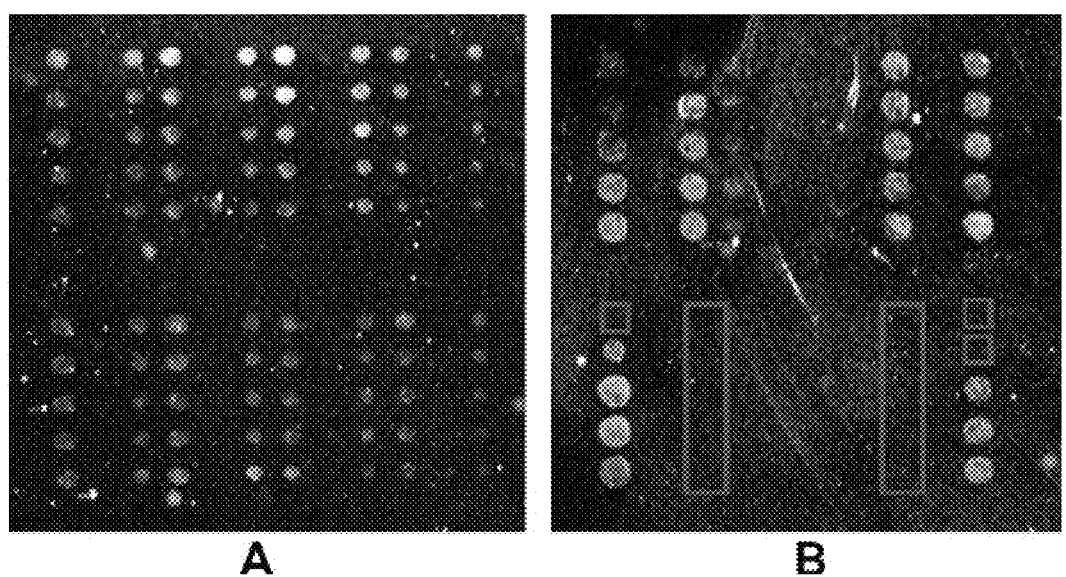
FIG. 4A is a scanned image of a bad-spotted DNA microarray stained with nanogold particles, showing some spots on the array were not homogenous even though the concentration of the probes was the same.
FIG. 4B is a scanned image of a poorly-spotted DNA microarray stained with nanogold particles showing missing spots on the array.

When a DNA microarray is prepared by a spotter, poor-quality arrays can be made from defects in the spotting pins and/or inappropriate sample preparation. Currently, it is not easy to pinpoint these bad chips or spots in a chip after fabricating. Arrays fabricated without homology spots and/or with missing spots could be found with our approach. Examples are shown in FIGS. 4A and B. The defected arrays could be excluded from the hybridization process for quality control. Only well-spotted arrays were picked for hybridization. With our approach, the quality of a spotted array could be thoroughly examined after array fabrication. When the probe density distributions of these spots were well documented, these defected arrays could still be used, if necessary The quality of a DNA-spotted array was visible after array fabrication. Arrays fabricated without homology and with missing spots (FIGS. 4A and 4B) can be eliminated from subsequent experiments and only well spotted DNA arrays used for hybridization. This ability to cull all substandard arrays is essential for maintaining array quality control (array QC).

Example 9

Hybridization of Destained Arrays

Figure 6:
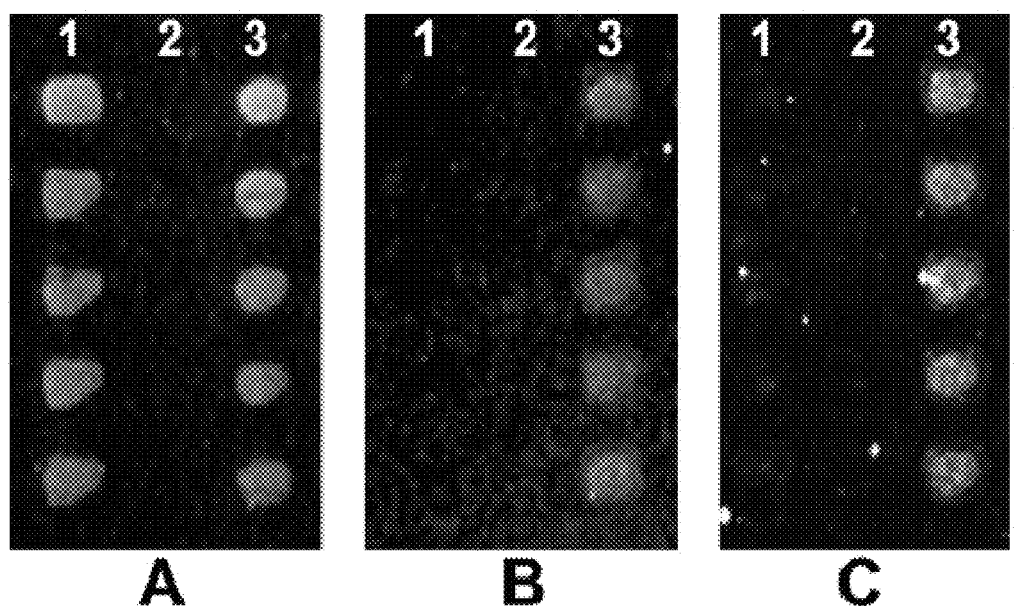
FIG. 6A is a scanned image of a DNA probe-immobilized microarray before hybridization that was stained with nanogold particles. Lane 1: control probe (TAF2Ht); lane 2; blank (spotting control, 50% DMSO); lane 3: target probe (PC101).
FIG. 6B is a scanned image of a DNA probe-immobilized microarray after hybridization that was stained with nanogold particles. The array had been treated with nanogold staining and dissolution before hybridization. Lane 1: control probe (TAF2Ht); lane 2; blank (spotting control, 50% DMSO); lane 3: target probe (PC101).
FIG. 6C is a scanned image of a DNA probe-immobilized microarray after hybridization that was stained with nanogold particles. The array had not been treated with nanogold staining and dissolution before hybridization. Lane 1: control probe (TAF2Ht); lane 2; blank (spotting control, 50% DMSO); lane 3: target probe (PC101).

Prehybridization treatment of a bromine-bromide solution was assessed. FIG. 6A shows the staining results of a DNA microarray before prehybridization. The array was stained by gold nanoparticles. Lane 1: control probe (TAF2Ht); lane 2: Blank (spotting control, 50% DMSO); lane 3: Target probe (PC101). The stained DNA microarray was then dissolved by bromine-bromide treatment to remove gold nanoparticles. After removal of nanogold staining, the same DNA array then performed hybridization and nanogold particle staining (FIG. 6B). FIG. 6A shows probe staining results of a DNA array before hybridization. FIG. 6B shows staining results of a DNA array after hybridization. In FIG. 6B, DNA array had been stained for probes and destained with HBr/Br2, and subsequently hybridized with DNA target. FIG. 6C shows the staining results of a DNA array that was hybridized directly. M13mp1, a phage DNA, was the complementary target of PC101, which was a probe design based on M13mp18.

To check the effects of gold staining and destaining on the hybridization process, we hybridized denatured target DNA to two separate arrays in the same condition. For comparison, the other DNA array was hybridized and stained with gold nanoparticles under the same condition but had not been treated with nanogold particle staining and dissolving process before the hybridization (FIG. 6C). Array prehybridization, hybridization, postwashing, and staining with gold particles were performed in the same condition. In the experiment, no obvious differences between these two arrays were observed (FIGS. 6B and C). Therefore, hybridization specificity was maintained without any effect from the dissolution of gold particles with bromine-bromide solution. This result confirmed that quality arrays could be obtained without compromising the quality of hybridization. Nanogold staining based on charge-charge interaction is reliable and simple for the characterization of DNA chips. Each hybridization spot on a chip could be characterized and documented. The nanogold on a stained DNA microarray could be dissolved with bromine-bromide treatment. The same array after destaining was subjected to hybridization and gold staining.

Example 10

Prehybridization Effect on Nanogold Staining

Array prehybridization is an important step in array hybridization. We also tried to check any effect of prehybridization on nanogold staining with a PC scanner detector. There are two main purposes for prehybridization. The first is to block the array surface with short DNA or other reagents so that nonspecific binding of DNA to the surface is reduced to a minimum. The second is to wash off nonimmobilized probes. Therefore, we pursued the effect of prehybridization on the staining process.

Figure 7:
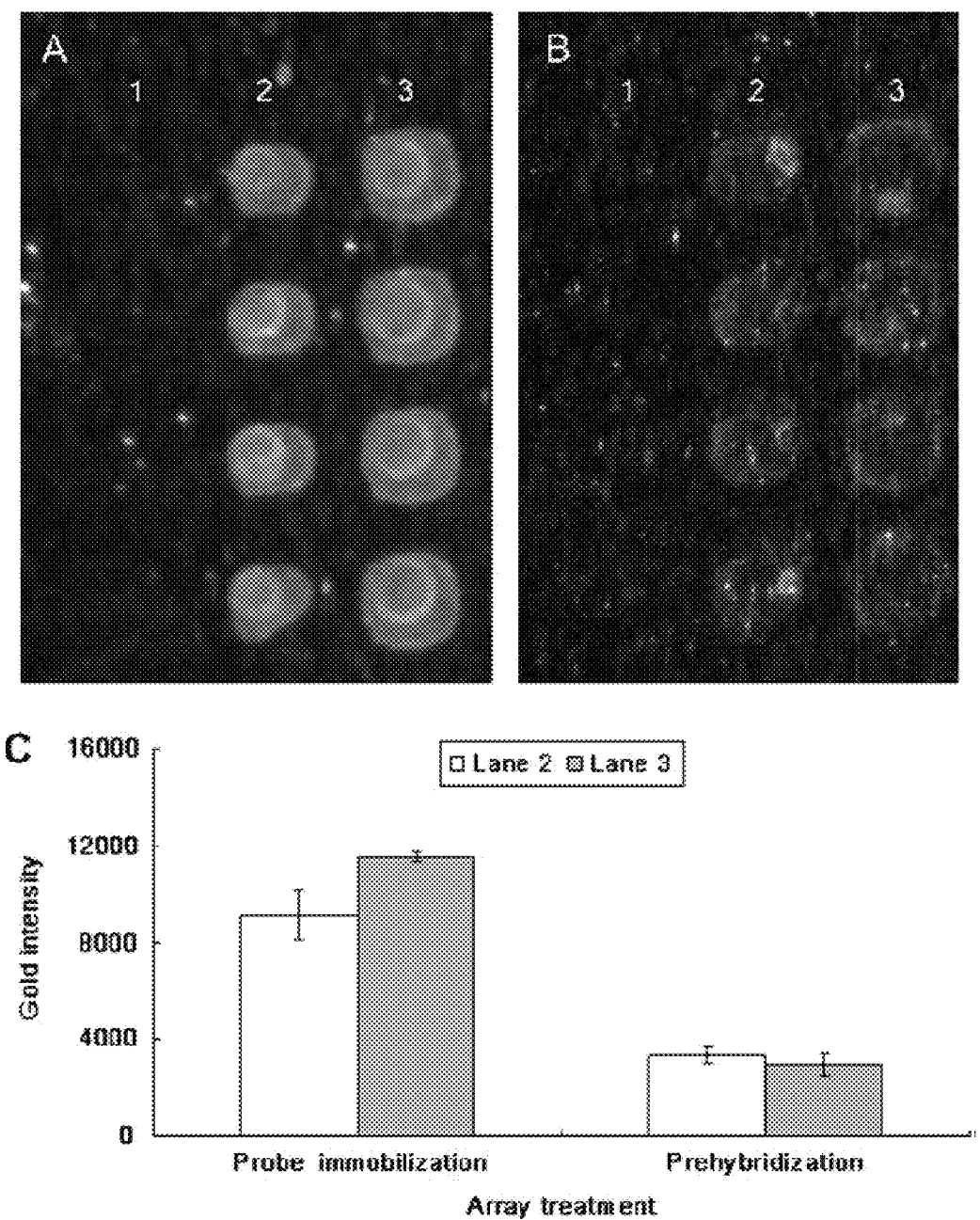
FIGS. 7A-7B show gold nanoparticle staining results of immobilized array (7A) and prehybridized array (7B) are shown. Panels shown in FIGS. 7A-7B were the same arrays that were stained by nanogold after probe immobilization.
FIG. 7C shows the intensity data of probes 2 and 3 corresponded to panels A and B. Lane 1: spotting with DMSO; lane 2: probe TAF2H (60mer) immobilized on the surface; lane 3: probe TAF2H-L (70mer).
Figure 8:
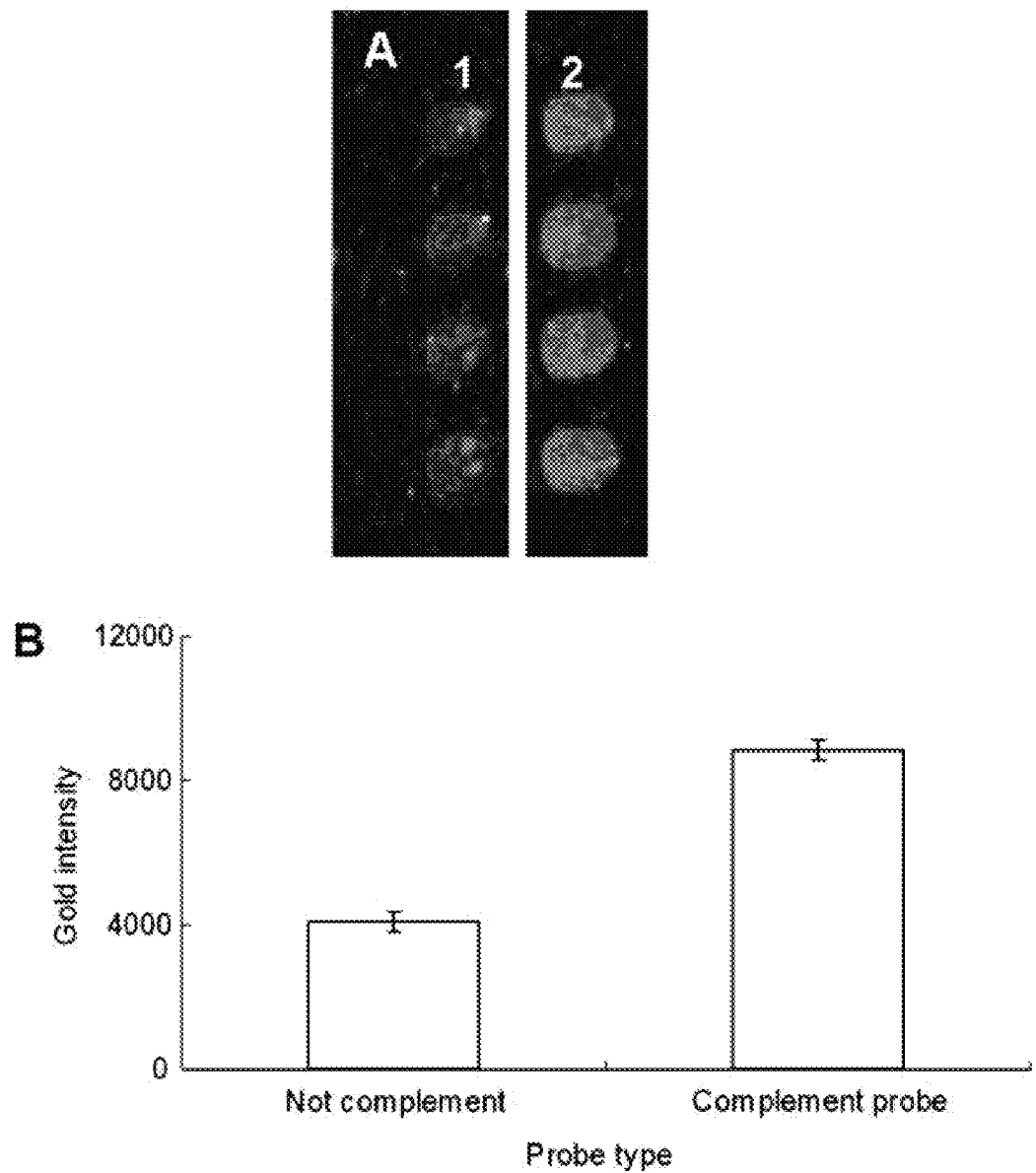
FIG. 8A shows gold nanoparticles staining results of an array hybridized with TAF2Ht. Lane 1: probe RPL6, which was not complementary to the target; lane 2: probe TAF2H, which was complementary to the target.
FIG. 8B shows the intensity data of probe 1 (not complement) and probe 2 (complement probe) corresponding to panel shown in FIG. 8 A.

We found that the spots stained by nanogold were weaker after prehybridization (FIG. 7). Two major reasons were that (i) some oligonucleotides immobilized on the slide surface may be washed off to pursue hybridization with probes and targets at similar oligonucleotide sizes (FIG. 8). After hybridization was completed, signals from the complementary probe were approximately a factor of 2 of those from the noncomplementary probe (FIG. 8). This indicated that the signal reduction was mostly from the washout process on some probes that were weakly bound to the surface rather than from the change of electric charge. This result could also be used to explain the much weaker signals for the spots with noncomplementary probes (FIG. 2) compared with the corresponding spots (FIG. 1).

One of the concerns about using nanogold labeling based on charge-charge interaction is the potential background from probe oligonucleotides that may reduce the distinction between hybridized spots and nonhybridized spots. In FIGS. 6B and C, we observed a high distinction between signals from complementary and noncomplementary hybridization because the length of the target DNA was much longer than that of the probe DNA. With nanogold labeling using charge-charge interactions, we found that it was highly preferable to have target nucleic acids much longer than the probe DNA. Therefore, for long probes, such as those used for cDNA arrays, the signal-to-noise ratio will be worse with this approach.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. A method for selecting a microarray suitable for performing specific binding reactions, wherein the microarray suitable for performing the specific binding reactions meets a predetermined quality standard, the method comprising the steps of:
    (a) performing a staining interaction by contacting microarrays with a solution comprising detectable cationic gold nanoparticles under conditions, wherein biomolecules are immobilized at discrete locations on the surface of each of the microarrays, wherein the detectable cationic gold nanoparticles are able to reversibly stain the biomolecules through an electrostatic interaction, and wherein the conditions comprise suitable solution pH and suitable solution ionic strength for staining the biomolecules with the cationic gold nanoparticles, thereby forming stained microarrays comprising the cationic gold nanoparticles;
    (b) detecting a visible staining signal from the cationic gold nanoparticles on the stained microarrays after the staining interaction, wherein the predetermined standard of quality is selected from the group consisting of: a stained microarray from the stained microarrays has an uniform intensity of the visible staining signal at each of its discrete locations and a stained microarray from the stained microarrays has an uniformity of the visible staining signal at various locations, and
    (c) selecting a microarray that meets the predetermined quality standard from the stained microarrays as the microarray suitable for performing the specific binding reactions.

2. The method of claim 1, wherein the biomolecules are selected from the group consisting of: DNA, RNA, oligonucleotides, peptides, proteins and biopolymers.

3. The method of claim 1, wherein said detecting the visible staining signal comprises scanning the stained microarrays.

4. The method of claim 1, further comprising: selecting a microarray which meets the predetermined standard of quality from the stained microarrays for destaining;
    destaining the microarray that meets the predetermined quality standard selected from the stained microarrays using a bromine-bromide solution and forming a destained microarray.

5. The method of claim 4, further comprising:
    (d) performing the specific binding reactions using the destained microarray that meets the predetermined quality standard.

6. The method of claim 1, wherein the stained microarrays with a lack of homology spots of the visible staining signal and the stained microarrays with missing spots of the visible staining signal at their one or more locations from the stained microarrays are eliminated for subsequent experiments due to failing the predetermined quality standard.

7. A method for selecting a nucleic acid microarray suitable for performing a hybridization reaction with a target nucleic acid, wherein the microarray suitable for performing the hybridization reaction with the target nucleic acid meets a minimum quality standard, the method comprising the steps of:
    (a) contacting microarrays with a solution comprising cationic gold nanoparticles under conditions, wherein nucleic acid probes are immobilized at discrete locations on the surface of each of the microarrays, wherein the cationic gold nanoparticles reversibly stain the nucleic acid probes, wherein each of the nucleic acid probes is at least 50 nucleotides in length, and wherein the conditions comprise suitable solution pH and suitable solution ionic strength for staining the nucleic acid probes with the cationic gold nanoparticles, thereby forming stained microarrays comprising the cationic gold nanoparticles;
    (b) detecting a visible staining signal from the cationic gold nanoparticles on the stained microarrays by scanning the stained microarrays, thereby selecting a microarray that meets the minimum quality standard, wherein the minimum quality standard is selected from the group consisting of: a stained microarray from the stained microarrays has an uniform intensity of the visible staining signal at each of its discrete locations, and a stained microarray from the stained microarrays has an uniformity of the visible staining signal at its various locations; and
    (c) obtaining destained microarrays by destaining the stained microarray and selecting a nucleic acid microarray suitable for performing the hybridization reaction with the target nucleic acid from the destained microarrays.

8. The method of claim 7, further comprising:
    (e) performing a hybridization reaction using the target nucleic acid and one of the destained microarrays that meets the minimum quality standard.

9. The method of claim 8, wherein the sizes of the nucleic acid probes immobilized on the microarrays are at least 2× shorter than the target nucleic acid used in the hybridization reaction.

10. The method of claim 8, further comprising a step of performing a prehybridization reaction before the hybridization reaction.

11. The method of claim 7, wherein said destaining the stained microarray is performed using a bromine-bromide solution.

12. The method of claim 11, wherein the bromine-bromide solution is about $10^{-4}$ M $Br_2$ in about 1M HBr.

13. The method of claim 7, wherein the nucleic acids are selected from the group consisting of DNA, RNA, microRNA, dsRNA, small interfering RNA (siRNA), oligonucleotide, and synthetic oligonucleotide.

14. The method of claim 7, wherein the cationic gold nanoparticles comprises positively charged gold nanoparticles comprising amino groups on their surfaces.

15. The method of claim 7, wherein the stained microarrays with a lack of homology spots of the visible staining signal and the stained microarrays with missing spots of the visible staining signal at their one or more locations from the stained microarrays are eliminated for subsequent experiments due to failing the minimum quality standard.

* * * * *